US007818182B2

(12) United States Patent
Giraldo et al.

(10) Patent No.: US 7,818,182 B2
(45) Date of Patent: Oct. 19, 2010

(54) ENDOSCOPE MANAGEMENT SYSTEM

(75) Inventors: Carlos A. Giraldo, Scarborough (CA);
Michael T. Small, Mississauga (CA);
Chadi Ismail, Mississauga (CA)

(73) Assignee: Endologistics Inc., Toronto, Ontario (CA)

( * ) Notice: Subject to any disclaimer, the term of this patent is extended or adjusted under 35 U.S.C. 154(b) by 701 days.

(21) Appl. No.: 11/841,471

(22) Filed: Aug. 20, 2007

(65) Prior Publication Data
US 2009/0055215 A1    Feb. 26, 2009

(51) Int. Cl.
G06Q 10/00 (2006.01)
G06F 19/00 (2006.01)
A61B 5/00 (2006.01)
A61B 18/18 (2006.01)

(52) U.S. Cl. ............... 705/2; 705/3; 705/28; 600/300; 606/46

(58) Field of Classification Search .......... 705/2–3, 705/28; 600/300; 606/46
See application file for complete search history.

(56) References Cited
U.S. PATENT DOCUMENTS
6,112,502 A * 9/2000 Frederick et al. .............. 53/411

6,223,137 B1 * 4/2001 McCay et al. ............... 702/184
2006/0218026 A1 * 9/2006 Osborne ........................ 705/8
2009/0272806 A1 * 11/2009 Kemp et al. ............... 235/462.1

FOREIGN PATENT DOCUMENTS
WO    WO 95/27252 A1 *  3/1995

* cited by examiner

Primary Examiner—Robert W Morgan
Assistant Examiner—Joseph Burgess
(74) Attorney, Agent, or Firm—Baker & McKenzie LLP

(57) ABSTRACT

A web-based endoscope management system and method for managing, scheduling and tracking in real-time the processing of endoscopy equipment in a single site or across multiple sites. The system allows various useful information relating to the managed endoscopy equipment and its processing history (such as equipment status, equipment movement, equipment repair history, cost and procedural efficiencies, what individuals have processed or come into contact with the equipment) to be tracked and analyzed. The system incorporates a user display and prompt to assist users in following the proper processing and cleaning protocols (preparation, pre-cleaning, automated reprocessing, repair, etc.) for the equipment. The system uses a color-coded display so that pertinent information can be seen at a glance. This system is used in conjunction with a suitable color-coded labeling scheme to reduce the possibility that users will process the wrong equipment or improperly store it.

5 Claims, 2 Drawing Sheets

ENDOSCOPE MANAGEMENT SYSTEM

FIELD OF THE INVENTION

Disclosed herein is an invention relating to a system for managing the processes and equipment of an endoscopy suite. More particularly, disclosed herein is a computer-based system for tracking, scheduling and analyzing operational procedures and the use of endoscopy-related equipment, for analyzing cost and procedural efficiencies thereof, and for enforcing standardization of procedures relating to endoscopy-related equipment in a medical facility. The system enforces the standardization of cleaning and infection control protocols promoting a high degree of patient safety. The system can be used in a single hospital site or can be used to manage multi-site environments where it becomes an enterprise management system, in each case, providing a centralized management system, enabling easy accumulation of any required information.

BACKGROUND

In a hospital or clinic setting, the use of endoscopes and related equipment is very common, both during surgical (therapeutic) procedures and for diagnostic purposes. Disclosed herein is a sophisticated tracking tool allowing endoscopy suites to trace in real-time numerous useful parameters/information in the daily processing cycle within an endoscopy suite, such as equipment movement (i.e. where is each piece of equipment current located, where is it scheduled to be), equipment cleaning procedures, equipment repair and maintenance procedures, equipment status (i.e. is the equipment currently being used for a medical procedure, is it being cleaned or repaired), how often equipment is in use, how frequently certain equipment has to be repaired or is offline, repair spending for each piece of equipment, overall repair/spending patterns and the people who have been responsible for processing of or who have otherwise come into contact with each piece of equipment (technicians, medical staff and/or patients). This information tracking functionality can be utilized in conjunction with a scheduling function for scheduling, for example, patients, endoscopy equipment and an available operating room. Although the disclosed system is discussed herein with reference to endoscope suites and endoscopy-related equipment, it should be appreciated that the system may readily be adapted and used for other types of medical equipment, particularly in those instances where traceability of equipment is of concern. The disclosed system seeks to automate a number of current manual processes, and by doing so, can effect time savings, cost efficiencies, and improvements in the level of safety and patient care. The disclosed system integrates and ties together the various daily operations of the endoscopy suite, such as the cleaning procedures, repair and maintenance procedures and patient scheduling. Currently, there are no systems that provide such integration. Further, the system does not require that all the endoscope equipment being managed be made by the same manufacturer; the system can concurrently manage multiple makes and models of endoscopy equipment together, as well as any equipment on loan or consignment from vendors.

In addition to tracking endoscopes the system incorporates a module that enhances infection control through monitoring the automated endoscope reprocessors (AERs) which are used to clean the endoscope equipment. This includes tracking the required maintenance and testing of the equipment to ensure they are meeting efficacy requirements needed to guarantee the effective cleaning of the endoscopes.

The disclosed system further is readily scalable and allows for multi-site operations to be managed from a central location thus enabling effective use of all resources (management, inventory use) across the multiple sites.

A prior art system is known which allows users to keep track of the number of times an endoscope has been used by means of a counter; however, this has rather limited application and does not provide the level of sophistication of the disclosed system. This prior art system is very primitive and only counts, when the endoscope is plugged in, how many times it is used. It is a manual system for which the "counter" can only be viewed on the particular endoscope when it is in use (by manually triggering a function command). Information is only accessible to the one individual actually using the endoscope and only when such endoscope is in use (i.e.: it has to be manually plugged in). In contrast, the disclosed system is a real-time, Internet/web-based system, enabling up-to-date information to be viewed from any location at any time. The disclosed system tracks, among other things, the actual amount of time an endoscope is used (not just how often). Prior art endoscope systems are also known which incorporate a scheduling function; however, these are focused on facilitating the medical procedures, particularly from the perspective of the doctors using the endoscope. This does not provide the broad functionality of the disclosed system, nor the endoscope-centric focus. These scheduling systems require users to manually enter the start and end of the procedure and only record when an endoscope is in use in the procedure. In contrast, the disclosed system tracks an endoscope throughout the entire processing cycle; it only requires a user at each stage to scan an endoscope in order for the relevant information to be automatically populated and for the endoscope to be moved to the next step in the process. The scheduler is automatically transitioned to the next applicable stage (e.g. typical stages/status are "scheduled" (coded red colour), "started" (coded blue colour), or "completed" (coded green colour)).

SUMMARY OF THE INVENTION

Described herein is a web-based computer system for tracking, scheduling and analyzing the operational procedures and use of endoscopy-related equipment in a medical facility or clinic.

The system is designed to be highly user-friendly in operation. It is relatively easy to set up the system and to update changes thereto (e.g. to add new equipment to an endoscopy suite's inventory of equipment). Information that is useful to a user can readily be tracked. Such information may be useful for a number of different purposes, including for operational efficiency purposes, budgetary purposes and infection control purposes. Further, any such tracked information can readily be made available to a user by use of sophisticated database/software query tools, either on a real-time basis or in the event a user wishes to conduct an analysis of the endoscopy suite over a specific period of time. In addition, the system is designed such that information that is presented to a particular user is easy to read and readily accessible.

Although for ease of explanation, the disclosed system is generally described herein as managing an endoscopy suite situated at a single medical facility (i.e. as a single-site system), it should be understood that the disclosed system is readily scalable and allows multiple sites to be managed and tracked from a central location. This greatly facilitates the effective management of multi-site facilities. Deploying the system across multiple sites and managing such sites from a single location provides for even greater opportunities for improving efficiencies.

The disclosed system is an Internet/web-based system. The system will incorporate suitable user display units which can facilitate the processing of the endoscopy equipment by providing pertinent information to the user or by giving on screen prompts. Preferably, some or all of the user display units will be in the form of medical grade touch screen panel PCs, used in combination with bar code scanners. A colour-coded presentation/display system is utilized to enhance the system's on-screen readability to a user. In a preferred embodiment of the system, this colour-coded display system is used in conjunction with a colour-coded labeling system either on the endoscopes themselves or on the hangers and/or storage cabinets for such endoscopes and related equipment, thus allowing for ease of identification and access to equipment and ensuring proper and safe storage (and also reducing the possibility that users may use or otherwise process the wrong endoscope by mistake).

BRIEF DESCRIPTION OF THE DRAWINGS

Reference is made to the following descriptions taken in conjunction with the accompanying drawings.

DETAILED DESCRIPTION OF THE INVENTION

Figure 1:
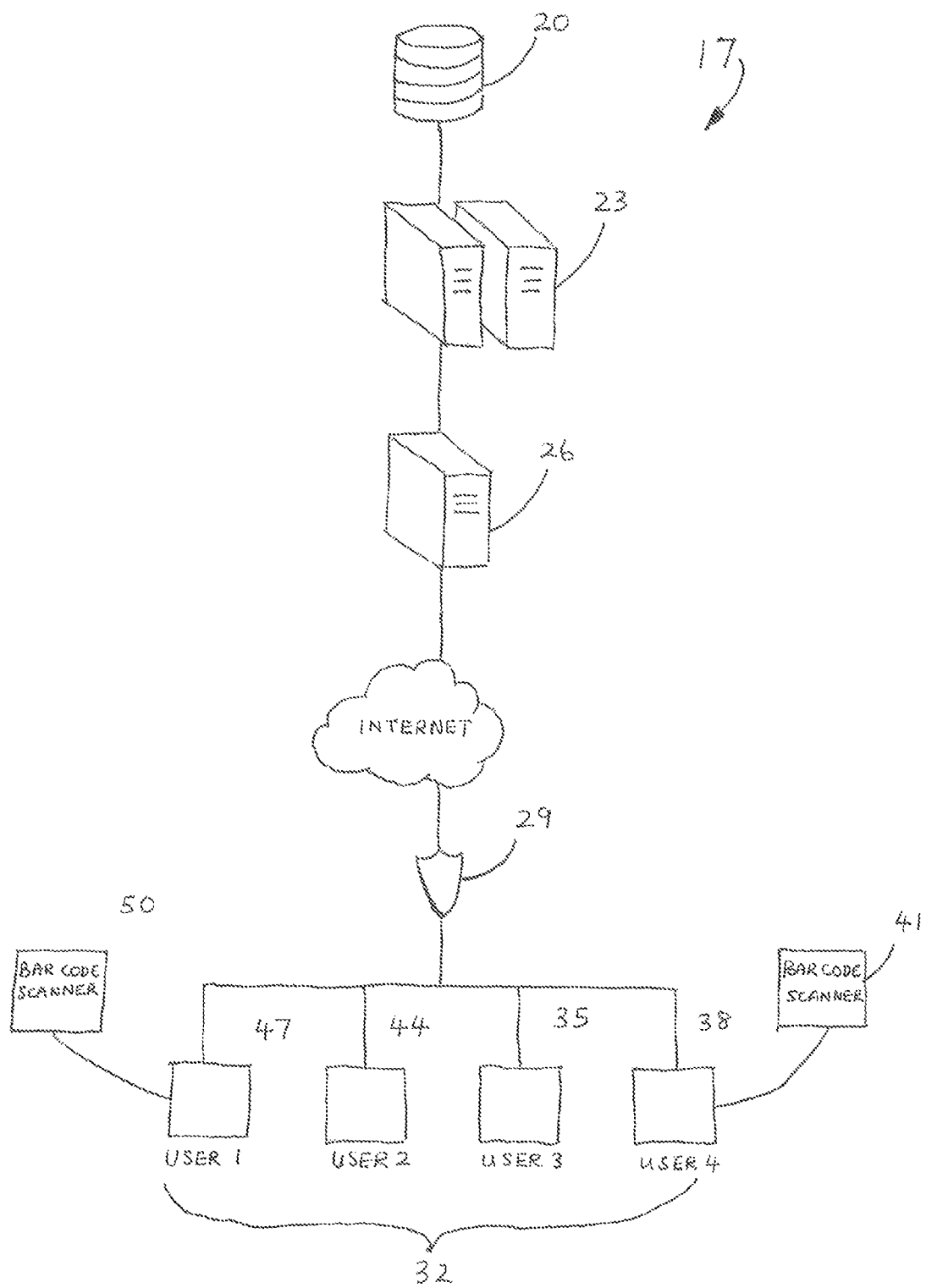
FIG. 1 is a graphical representation of the disclosed system.

Referring to FIG. 1, an endoscopy management system 17 is represented. The endoscopy management system (sometimes referred to herein as "EMS") 17 comprises various components, including a database 20 that resides on the EMS, a dedicated server 23, which in turn is in communication (it should be understood that communication may be by wired means or wirelessly) with a web server 26. The dedicated server 23 hosts the endoscopy management system application, i.e. the software component of the endoscopy management system 17. In one embodiment of the disclosed system, the endoscopy management system application is a software program written in ASP.Net where the database resides on an SQL server. The web server 26 communicates via the Internet with certain networked component units of the on-site computer equipment 32 of the endoscopy management system which are located at a medical facility (sometimes referred to herein as "computing terminals"). To protect the integrity and confidentiality of the data/information that is transmitted between the medical facility and the web server 26 via the Internet, the information is generally encrypted (e.g. using high security 256-bit data encryption techniques).

By way of example only, the on-site computing terminals 32 may comprise at least one personal computer or computer workstation 35, which has access to the Internet through which it communicates with the dedicated server 23. As illustrated in FIG. 1, the networked on-site computing terminals 32 can also comprise at least one touch screen personal computer 38 ("PC"), preferably a medical grade touch screen panel. Such touch screen panels allow for ease of use and are easy to clean. The touch screen PC 38 is communicatively linked to a bar code scanner 41. The bar code scanner 41 can, for example, utilize LS-9208 bar code technology, and when the system is in use, will typically be situated in an operating room or any other location where an endoscope may be processed. Also shown in FIG. 1, is a PC or computing terminal 44 which, for example, can provide information relating to and which facilitates management of medical and technical personnel (a "staff manager"). Alternatively, PC or computing terminal 44 can manage or track other functions such as the cleaning, maintenance or repair of equipment. Communicatively linked to PC 44 is shown at least one touch screen PC 47 (again, preferably a medical grade touch screen panel), which can be situated, for example, in an equipment cleaning room. The touch screen PC 47 is communicatively linked to a bar code scanner 50.

Once a new piece of endoscopy equipment is acquired by a medical facility which is running the disclosed system, it is added into the inventory of managed equipment. The set-up procedure involves providing each piece of equipment with an identification serial number or bar code tag. Various other parameters or information for the piece of equipment can be inputted into the system, according to the types of attributes that are considered useful to have available or to keep track of, such as model type and number, the service provider/manufacturer, purchase date, purchase status (i.e. whether an endoscope is owned, borrowed from another department/facility, or on loan or consignment from any manufacturer), the applicable cleaning protocols (including validation periods (since certain scopes have requirements on tracking shelf life or idle time between cleaning cycles) for the endoscope, repair status, warranty or contract coverage, and purchase cost. In the diagram of FIG. 1, the set-up procedure would typically be carried out on PC 35. During the initial set-up of the system itself, other parameters or information would also typically be entered into the system, such as the number of operating and cleaning room locations, identification #s for each member of the medical staff, etc., so as to facilitate the tracking of pertinent information.

When the endoscopy management system 17 is in operation, it can utilize its scheduling functions programmed into the endoscope management application to schedule the applicable medical procedures. For example, it can schedule certain endoscopy equipment according to the medical procedure that is scheduled, provided the appropriate equipment is available, and assign an operating room for carrying out the medical procedure. Technicians can utilize this information to deliver the appropriate endoscopy equipment to the proper location and/or prepare the equipment for the next scheduled medical procedure. Such scheduling functions can take place well ahead of time (e.g. the day before) or in real-time (e.g. as equipment, operating rooms, etc. get freed up and become available). Furthermore, these scheduling functions can be used in conjunction with the medical facility's other patient scheduling capabilities so as to act as an additional "checks and balance" level or they can be completely integrated into a single patient/operation scheduling module. Departments such as "patient recovery", can access the relevant information enabling them to know when a procedure is being carried out or completed and have bed space available and be prepared to receive patients in a timely and effective manner. Administrative personnel are also able to view relevant information and keep family members apprised as to the status of a patient's procedure (without interrupting other staff members).

After the attributes of a particular endoscope have been entered into the system, the endoscope can readily be identified to the system once its bar code tag has been scanned by a bar code scanner 41. The user can be provided with certain instructions or prompted for relevant information (such as verification of operating room#, patient particulars, etc.) via the touch screen PC 38. All users handling the endoscopy equipment will also be asked to identify himself/herself to the system, by entering their unique user ID in to the system or by scanning her own identification bar code tag. As information is entered into the system or updated, it is communicated via the Internet to the endoscopy management system application hosted on the dedicated server 23. The information is maintained on the endoscopy management system application or, where applicable, stored on the database. Such information can be updated almost instantaneously, thus allowing information to be tracked in real-time. In a similar fashion, as shown in FIG. 1, other bar code scanners 50 and corresponding touch screen PCs 47 can be provided at each other location, such as at an endoscope cleaning room, so that the movement of each piece of endoscopy equipment within the medical facility (as well as its current location) can be tracked. The entering of unique user IDs is required at all key process points throughout the entire processing cycle of the endoscope. This encourages a system of accountability and accuracy while also facilitating the tracking of employee efficiencies.

Any tracked information or any other information that has been captured by the system can be made available to a user (provided they have the appropriate authority to access such information), e.g. through any of the computing terminals 32. This can include real-time information, such as how many endoscopes are currently available for operation, where are they located or how many endoscopes are not in use (e.g. being cleaned or being repaired). More detailed information (including historical information) can also be determined using software-based reporting or database query tools, allowing users or administrators to conduct analyses regarding the operational efficiency of the endoscopy suite, repair history of each piece of equipment, etc. Information such as capital spending, repair cost, frequency of repair, and average useful life of particular models of endoscopy equipment can also be analyzed for budgetary and planning purposes; the most cost-effective or robust models of endoscopy equipment can readily be determined and operating cost comparisons between different endoscopes, service providers and manufacturers can be facilitated.

By way of example only, such reporting and analysis tools can be critically useful for purposes of infection control. Where an endoscope has been used, and it is later discovered that the endoscope was not properly cleaned or the patient was found to have a highly infectious disease, it is fairly straightforward to quickly locate the impugned endoscope and remove it for cleaning or additional processing, and to analyze which patients, medical personnel, technicians and AERs may have come into contact with the particular endoscope. Alternatively, if an issue has been detected with a particular AER, all endoscopes and patients affected can be quickly and easily identified. This allows for better risk management and quick development of corrective actions.

Figure 2:
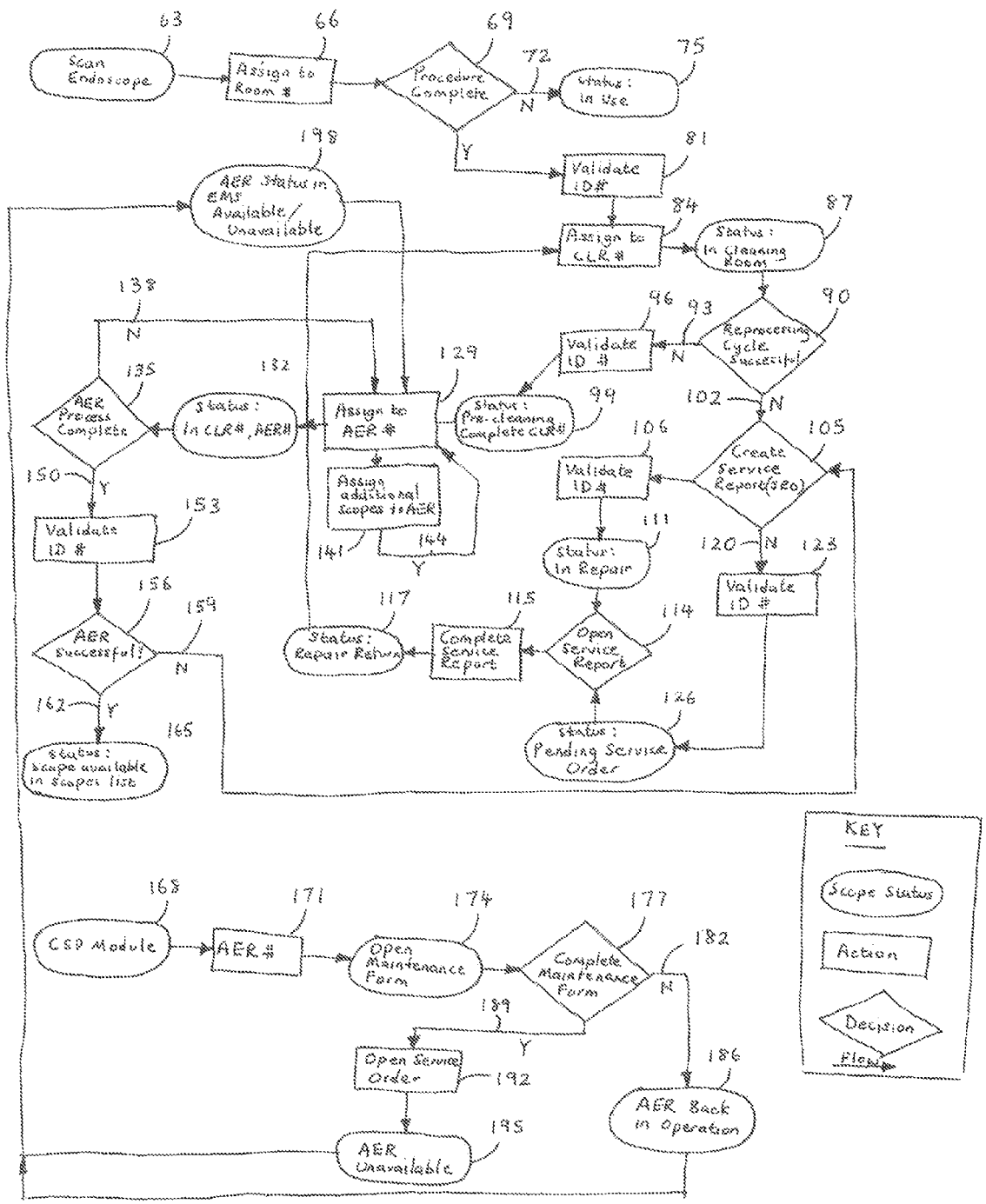
FIG. 2 is a flowchart illustrating the process flow of the disclosed system.

FIG. 2 is a flowchart illustrating an exemplary process flow for an endoscope within the disclosed system. The programming logic associated with the various functionalities of the endoscopy management system application (such as for scheduling, processing, etc.) have not been described in detail, but would be readily understood by one skilled in the art. Although not expressly described in the process flow description below, at each applicable processing stage or where there is a change in status or endoscope information, the information can be uploaded to the endoscopy management system application and updated accordingly. Firstly, an endoscope is scanned and identified to the system (step 63). The endoscope (and the medical procedure to be carried out therewith) is assigned to a certain operating room (step 66) (this step involves a user simply verifying that the correct endoscope has been assigned to the correct room #). Once the medical procedure has been initiated (steps 66 and 69), the endoscope is designated a status of "In Use" (step 75). When the medical procedure is complete, the endoscope is scanned and the user's identity verified (step 81). The endoscope is then assigned to a particular cleaning room for cleaning and pre-cleaning (step 84). At this stage, it is designated a status of "In Cleaning Room #" (step 87). If the endoscope is to be reprocessed for continued use (step 93), the user's identity is verified (step 96) and then the endoscope is designated a status of "Pre-Cleaning Complete CLR#" (step 99). If the endoscope is not to be sent on for reprocessing (step 102), it may be necessary to create a service report (step 105) and to enter a validation code (step 106), e.g. where the endoscope must undergo repairs (steps 108 and 111). When the necessary repair has been carried out (step 117), and the endoscope received in, the Service Report is opened (step 114) and completed as per invoicing (step 115). The repaired endoscope is given a status of "Repair Return" (step 117). The endoscope is reassigned for pre-cleaning to a cleaning room (step 84). Where the endoscope requires service but it is decided that a work order should not be assigned immediately (step 120), the user is prompted to enter a validation code (step 123) and the endoscope is scanned (step 123) and designated a status of "Pending Service Order CLR#" (step 126). This flags the endoscope for required follow up for a service report to be opened but the scope is made not available for use.

When the pre-cleaning process for the endoscope has been completed (step 99), the next stage is that it must be assigned for automated endoscope reprocessing (AER) in a particular automated endoscope reprocessing room (step 129). At this stage, the endoscope is designated a status of "In CLR#, AER#" (step 132). If AER is not completed, then the endoscope is sent back through the process again (step 138). During AER, multiple endoscopes can be simultaneously processed (step 141). Once AER is completed (step 150), the endoscope is scanned for verification purposes and the user validated (step 153). The endoscope can be checked and tested to determine whether the AER was satisfactory/successful (step 156). If not, it is further investigated to see whether a service report needs to be created therefor (step 105). If the AER was satisfactory/successful, then the endoscope is designated a status of "Available" meaning it can be assigned for further medical procedures.

It should be appreciated that the above merely illustrates an example of the process flow for the disclosed system and is not intended to be exhaustive. Additional steps may be provided as required. Further levels of checks and verification steps can be provided to increase the accountability of personnel handling the endoscopy equipment. Although not expressly mentioned in the above example, the applicable computing terminals 32 of the disclosed system will provide users with suitable on-screen prompts during the process flow, providing specific instructions or seeking verification of pertinent information or of personnel at each stage, as well as keeping a real-time scheduler that is updated throughout the working day as procedures are performed/completed (procedures are designated as "Scheduled", "In Process" or "Complete"). This greatly improves the processing and cleaning of the endoscopy equipment, as described in more detail below.

For each piece or suite of endoscopy equipment, a number of procedures are necessary to prepare such equipment for use on a patient; the equipment may need to be prepared or customized for particular surgical operations. Further, after the equipment has been used, a number of procedures are necessary to properly clean/treat the equipment. In addition, a number of procedures may also be required to maintain the equipment in good working order and to verify that it is fully operational. The nature and extent of required procedures are highly variable, and may be determined according to any of a number of factors, including: protocols recommended by the equipment manufacturer (e.g. preparation or cleaning protocols), protocols dictated by the hospital/clinic or medical staff, the type of endoscopy equipment, and the nature of the surgical procedure for which the equipment was used. There are a number of different endoscope equipment manufacturers, some or most of whom will recommend slightly different protocols, especially where different models of endoscopy equipment are involved. This difference in the preparation and cleaning procedures can be particularly problematic for hospital staff and technicians, since different procedures may be applicable in different circumstances. One aspect of the disclosed system is the ability to prompt the hospital staff/technicians as to the applicable preparation and cleaning procedures for each piece of endoscopy equipment and further to seek confirmation from the staff/technicians that the necessary procedures have been followed and completed. This facilitates the processing of the endoscopy equipment. The system can also provide for as many "checks and balances" to be introduced into the processing of the equipment as deemed necessary, and can provide for greater accountability of the persons that take part in the processing/cleaning of the endoscopy equipment.

To facilitate the ease of interpreting the information that is presented to a user, a colour-coded presentation/display system is utilized. The user can thus determine at a glance, for example, which endoscopes are available or out of order. In a preferred embodiment of the system, this colour-coded display system is used in conjunction with a colour-coded labeling system either on the endoscopes themselves or on the hangers and/or storage cabinets for such endoscopes and related equipment, thus allowing for ease of identification and ensuring proper and safe storage of the endoscope equipment. This also reduces the possibility that users may use or otherwise process the wrong endoscope by mistake.

The disclosed system integrates a number of other functionalities as outlined below. The system tracks whether a piece of endoscopy equipment is on-site or out for repair; and also tracks in real-time how long each piece of equipment is "out for repair" or otherwise not in service. The overall inventory of stock can be monitored, as well as their present locations. When there is a shortage in inventory of equipment, protocols can be put in place to automatically notify the relevant departments within the medical facility and/or to initiate acquisition of additional equipment (whether making requests to manufacturer (service provider) loaner or purchase programs or by in-house requisitions). The system has the capability to record and track all reprocessing and cleaning steps applied to each item of endoscopy equipment. Service orders can also be tracked to determine the status and efficiency of repair or maintenance procedures.

The Repair process in the disclosed system integrates the ability to process and e-mail information directly to service providers and/or other departments within the hospital (e.g. purchasing). The system incorporates quick links to pre-defined reports that can be programmed into the system for each service provider (e.g. loaner request forms, repair request forms, purchasing forms). Loaners requested for repairs are tagged and identified by a unique colour, enabling users to quickly identify why a loaner is in house, how long a repair has been out for, etc.

The disclosed system incorporates a "Special Inventory" (SI) classification that is used for identifying equipment on consignment (or loan) from vendors. This could include specialty endoscopes, long term loan equipment, demonstration equipment, equipment for clinical evaluation, etc. All equipment (customer, loaner, consignment, etc.) may be tracked through the system and treated in a similar fashion as described above. Queries for information can be done for all types of equipment.

The disclosed system is provided with a separate but integrated module called Central Services Department (CSD) used for tracking all Automatic Endoscope Reprocessors (AERs). This CSD module can be used or can sit idle, running in the background should users choose not to use this function. AERs require regular maintenance (i.e., cleaning, filters, fluid checks, fluid changes, etc.). CSD keeps track of all maintenance through a maintenance log and facilitates the filing of service reports in a manner similar to endoscopes. Should an AER go down or be in need of service, the AER will be duly flagged as such in the system, and the system will be prevented from assigning endoscopes to that particular AER for automated reprocessing. The process flowchart for this CSD module as described above is generally represented in FIG. 2. If an AER is flagged for possible maintenance (step 168), it is first identified to the system (step 171). If it is decided that a maintenance form should be completed for the particular AER (step 189), then a Service Order is opened (192) and the AER is flagged in the EMS system as being "Unavailable" (steps 195 and 198) and endoscopes can no longer be assigned by the system to that particular AER for reprocessing. If it is decided that a maintenance is not required to be completed, then the AER is flagged in the system as being "Back in Operation"/"Available" (steps 186 and 198).

The disclosed system incorporates three other independent modules that are used to capture pertinent information (primarily, patient information and inventory control) prior to, during and/or after each medical procedure, specifically: 1) Nursing Notes (for recording patient information, medication and vital signs, etc.); 2) Doctors' Information (having the functionality to capture pictures taken during the procedure and to record the physician's notes on the operation and follow-up required); and 3) Inventory Control (having the ability to monitor and track the purchase, usage and storing of all related ancillary consumable items used in an endoscopy setting (i.e., syringes, tubing, sterile fluids, bedding, masks, gloves, etc.). These three modules are integrated with the scheduler and facilitate easy and complete recall of required information as well as automatic re-scheduling should a patient require a follow-up procedure.

The disclosed system will incorporate an online Gastrointestinal (GI) chat line that will be aimed specifically at the GI community to facilitate the sharing of information and to aid in having specific questions addressed by fellow peers. Optionally, it is contemplated that this section will include a job bank, industry developments and technological advancements.

The system will also contain a database of companies in the endoscopy community. This will be a search engine for GI that will facilitate the finding of parts, accessories and the sellers for specific products needed in the hospitals, in particular in the endoscopy suite. The suppliers would provide online catalogues and advertise within the system enabling them to bring their products directly to the desk (computers) of their customers.

While various embodiments of the endoscopy management system have been described above, it should be understood that these have been presented by way of example only, and not limitation. Multiple inventions may be set forth according to the limitations of the multiple claims associated with this disclosure, and the claims accordingly define the invention(s), and their equivalents, that are protected thereby. In all instances, the scope of the claims shall be considered on their own merits in light of the specification.

What is claimed is:

1. A method for managing and tracking in real-time the processing of a plurality of endoscopes within a medical facility using an endoscopy management system, the method comprising:
   a) providing each one of the plurality of endoscopes with an identification serial and a corresponding identification bar code;
   b) storing endoscope information for each one of the plurality of endoscopes in a database;
   c) selecting an assigned endoscope for performing a medical procedure from an inventory of available endoscopes;
   d) scanning the assigned endoscope to be used for the medical procedure with a bar code scanner to identify said assigned endoscope to the endoscopy management system and updating the endoscope information accordingly;
   e) assigning the medical procedure to an available operating room and updating the endoscope information accordingly;
   f) arranging to have an assigned first user having an identification tag to perform the medical procedure using the assigned endoscope and updating the endoscope information accordingly;
   g) validating the identity of the assigned first user performing the medical procedure when the procedure is complete by scanning the identification tag of the assigned first user and updating the endoscope information accordingly;
   h) assigning the endoscope to an available cleaning room for pre-cleaning and updating the endoscope information accordingly;
   i) arranging to have an assigned second user having an identification tag perform the pre-cleaning procedure on the endoscope and updating the endoscope information accordingly;
   j) validating the identity of the assigned second user performing the pre-cleaning procedure when the procedure is complete by scanning the identification tag of the assigned second user and updating the endoscope information accordingly;
   k) assigning the endoscope to an available automated endoscope reprocessor for automated endoscope reprocessing and updating the endoscope information accordingly;
   l) having the endoscope undergo automated endoscope reprocessing and updating the endoscope information accordingly;
   m) arranging to have an assigned third user having an identification tag validate the satisfactory completion of the automated endoscope reprocessing by scanning the identification tag of the assigned third user and updating the endoscope information accordingly;
   n) returning the endoscope to the inventory of available endoscopes and updating the endoscope information accordingly; and
   o) repeating steps c) to n) for each additional endoscope for each additional medical procedure, as required.

2. The method of claim 1, wherein step i) comprises:
   having the pre-cleaning procedure performed on the endoscope and updating the endoscope information accordingly;
   arranging to have an assigned fourth user having an identification tag perform required service or repair on the endoscope where the pre-cleaning is not satisfactorily completed and updating the endoscope information accordingly;
   validating the identity of the assigned fourth user performing the service or repair when the service or repair is complete by scanning the identification tag of the fourth user and updating the endoscope information accordingly; and
   resuming the method of claim 1 from step h).

3. The method of claim 1, wherein at least one of the respective users are provided with prompts via a touch screen panel communicatively linked to the endoscopy management system with information to assist the users with proper processing of the endoscope.

4. The method of claim 3, wherein the information provided to the respective users is information relating to endoscope cleaning protocols.

5. The method of claim 1, wherein the endoscopy management system is adapted for communication with a plurality of networked onsite computing terminals and wherein users desiring to have access to the endoscope information access such information via the computing terminals.

* * * * *